United States Patent

Brazzell et al.

[11] Patent Number: 5,578,638
[45] Date of Patent: Nov. 26, 1996

[54] TREATMENT OF GLAUCOMA AND OCULAR HYPERTENSION WITH $\beta_3$-ADRENERGIC AGONISTS

[75] Inventors: Romulus K. Brazzell, New City, N.Y.; Bernard Dubnick, Westwood, N.J.

[73] Assignee: American Cyanamid Company, Wayne, N.J.

[21] Appl. No.: 148,154

[22] Filed: Nov. 5, 1993

[51] Int. Cl.$^6$ .......................... A61K 31/335; A61K 31/42; A61K 31/35
[52] U.S. Cl. .......................... 514/463; 514/376; 514/450; 514/451
[58] Field of Search .................................. 514/463, 376, 514/450, 451

[56] References Cited

U.S. PATENT DOCUMENTS

| | | | |
|---|---|---|---|
| 4,309,443 | 1/1982 | Smith et al. | 424/319 |
| 4,329,358 | 5/1982 | Ainsworth et al. | 424/309 |
| 4,338,333 | 7/1982 | Ainsworth et al. | 424/309 |
| 4,341,793 | 7/1982 | Ferris | 424/279 |
| 4,382,958 | 5/1983 | Duckworth | 424/330 |
| 4,385,066 | 5/1983 | Ainsworth et al. | 424/309 |
| 4,391,826 | 7/1983 | Mills et al. | 424/324 |
| 4,432,993 | 2/1984 | Ferris | 424/285 |
| 4,568,691 | 2/1986 | Marsham et al. | 514/443 |
| 4,585,796 | 4/1986 | Alig et al. | 514/620 |
| 4,588,749 | 5/1986 | Ferris | 514/649 |
| 4,593,023 | 6/1986 | Hindley | 514/233 |
| 4,596,800 | 6/1986 | Ainsworth et al. | 514/233 |
| 4,602,044 | 7/1986 | Schmiegel et al. | 514/653 |
| 4,622,342 | 11/1986 | Cantello et al. | 514/653 |
| 4,629,737 | 12/1986 | Cantello | 514/564 |
| 4,652,679 | 3/1987 | Alig et al. | 564/86 |
| 4,654,371 | 3/1987 | Ainsworth et al. | 514/555 |
| 4,683,312 | 7/1987 | Dominianni et al. | 548/341 |
| 4,692,465 | 9/1987 | Hindley et al. | 514/539 |
| 4,695,580 | 9/1987 | Ohashi et al. | 514/412 |
| 4,707,497 | 11/1987 | Cecchi et al. | 514/647 |
| 4,772,631 | 9/1988 | Holloway et al. | 514/539 |
| 4,783,460 | 11/1988 | Cantello | 514/233.5 |
| 4,803,293 | 2/1989 | Berge et al. | 560/42 |
| 4,871,755 | 10/1989 | Alig et al. | 514/376 |
| 4,892,886 | 1/1990 | Alig et al. | 514/567 |
| 4,927,836 | 5/1990 | Holloway et al. | 514/620 |
| 4,977,148 | 12/1990 | Holloway et al. | 514/183 |
| 4,992,473 | 2/1991 | Anderson et al. | 514/653 |
| 4,999,377 | 3/1991 | Caulkett et al. | 514/507 |
| 5,017,619 | 5/1991 | Alig et al. | 514/653 |
| 5,045,567 | 9/1991 | Kienzie | 514/539 |
| 5,061,727 | 10/1991 | Bloom et al. | 514/465 |
| 5,153,210 | 10/1992 | Ainsworth et al. | 514/369 |
| 5,166,218 | 11/1992 | Alig et al. | 514/652 |
| 5,202,466 | 4/1993 | Boigegrain et al. | 560/45 |
| 5,510,376 | 4/1996 | Epstein et al. | 514/463 |

FOREIGN PATENT DOCUMENTS

| | | |
|---|---|---|
| 0061907 | 10/1982 | European Pat. Off. |
| 0063004 | 10/1982 | European Pat. Off. |
| 0066351 | 12/1982 | European Pat. Off. |
| 0070133 | 1/1983 | European Pat. Off. |
| 0068669 | 1/1983 | European Pat. Off. |
| 0089154 | 9/1983 | European Pat. Off. |
| 0091749 | 10/1983 | European Pat. Off. |
| 0095827 | 12/1983 | European Pat. Off. |
| 0102213 | 3/1984 | European Pat. Off. |
| 0164700 | 12/1985 | European Pat. Off. |
| 0171702 | 2/1986 | European Pat. Off. |
| 0170121 | 2/1986 | European Pat. Off. |
| 0196849 | 10/1986 | European Pat. Off. |
| 0254856 | 2/1987 | European Pat. Off. |
| 0233686 | 8/1987 | European Pat. Off. |
| 0262785 | 4/1988 | European Pat. Off. |
| 0386603 | 9/1990 | European Pat. Off. |
| 0386920 | 9/1990 | European Pat. Off. |
| 0500443 | 8/1992 | European Pat. Off. |
| 0516349 | 12/1992 | European Pat. Off. |
| 0556880 | 8/1993 | European Pat. Off. |
| 61-145148 | 2/1986 | Japan. |
| 8400956 | 3/1984 | WIPO. |
| 8403278 | 8/1984 | WIPO. |
| 8404091 | 10/1984 | WIPO. |
| 9013535 | 11/1990 | WIPO. |
| 9218461 | 10/1992 | WIPO. |

OTHER PUBLICATIONS

Clark et al, *Chemical Abstracts*, vol. 104, No. 19, abstract #161536k, 1986, p. 15.
Investigative Opthalmology, pp. 455–457, Jun. 1974.
Pharmacological Basis of Therapeutics, Goodman & Gilman, Chapter 9, McMillan Publishing, NY 1980 (6th Ed.).
E.J. of Pharmacol., 100 (1984), 309–319.
Nature, vol. 309, pp. 163–165 (1984).
Current Eye Research, vol. 4, No. 7, pp. 775–780 (1985).
Brit. J. Pharmacol., 100:831–839 (1990).
Science, 245:1118–1121 (1989).

*Primary Examiner*—Marianne M. Cintins
*Assistant Examiner*—William R. A. Jarvis
*Attorney, Agent, or Firm*—Hedman, Gibson & Costigan

[57] ABSTRACT

This invention relates to a method of treating glaucoma or reducing intraocular pressure in a patient in need of such treatment which is based on the topical administration to the eye of a mammal or the systemic administration of a compound of the formula:

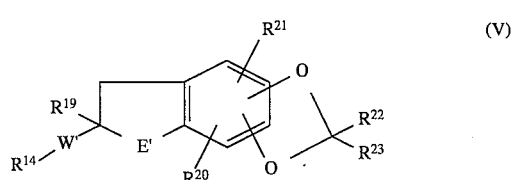

(V)

wherein E', W', and the R groups are defined in the disclosure.

2 Claims, 1 Drawing Sheet

TREATMENT OF GLAUCOMA AND OCULAR HYPERTENSION WITH $\beta_3$-ADRENERGIC AGONISTS

BACKGROUND OF THE INVENTION

1. Field of the Invention

The present invention relates to the use of $\beta_3$-adrenergic agonists for the treatment of glaucoma and ocular hypertension by topical or systemic administration in mammals. More particularly, it relates to the use of ophthalmological compositions containing an active amount of these $\beta_3$-agonists or the pharmaceutical acceptable salts thereof for the treatment of glaucoma and ocular hypertension.

2. Description of the Prior Art

Glaucoma is an ocular disorder that causes functional or organic disturbances in the eyes due to continuous or repeated increase in intraocular pressure. Not only is there an increase in intraocular pressure, but also optic nerve cupping and visual field loss. Although the pathophysiological mechanism of open angle glaucoma is still unknown there is substantial evidence to suggest that the increased intraocular pressure is detrimental to the eye and that it is the most important factor causing degenerative damage in the retina. Primary open-angle glaucoma is an insidious, slowly progressive, bilateral condition. The condition is often asymmetric on presentation, however, so that one eye may have moderate or advanced damage and the fellow eye has minimal or no detectable damage. Most patients with primary open-angle glaucoma have elevated intraocular pressures in the range of 22 to 40 mm Hg. The cardinal features of open-angle glaucoma include elevated intraocular pressure, cupping and atrophy of the optic disc, and visual field loss. Individuals with intraocular pressures of 21 mm Hg or greater, normal visual fields, normal optic discs, open angles, and the absence of any ocular or systemic disorders contributing to the elevated intraocular pressures are referred to as having ocular hypertension. The concept of ocular hypertension is important because this set of findings occurs in 4% to 10% of the population over age 40. The term normal-tension glaucoma refers to typical glaucomatous optic disc cupping and visual field loss in eyes that have normal intraocular pressures, open angles, and the absence of any contributing ocular or systemic disorders. Normal tension glaucoma may be a consequence of the retina being unusually sensitive to pressure and therefore damage may occur at intraocular pressure levels otherwise considered physiologically normal. The clinical features of normal-tension glaucoma resemble primary open-angle glaucoma except for the absence of elevated intraocular pressure. Some authorities believe the visual field and optic disc changes are identical in normal-tension glaucoma and primary open-angle glaucoma, whereas others state subtle differences exist between the finding of the two conditions. If left untreated, glaucoma almost invariably leads to blindness. The course of the disease is typically slow with progressive loss of vision. Conventional therapy for glaucoma is based on lowering the intraocular pressure, either by drugs, laser therapy, or surgery. The treatment of glaucoma is required to reduce an intraocular pressure to the level adequate to maintain normal optic nerve functions.

Pilocarpine eye drops have been used extensively for the treatment of glaucoma. It is known however that pilocarpine eye drops not only reduce intraocular pressure but also act on the iris sphincter muscle and the ciliary muscle thereby causing side effects such as pupillary constriction, accommodative spasm as well as conjunctival congestion. Such side effects may invite very serious dangers particularly to persons operating motor vehicles. In the case of an elderly patient with cataracts, miosis will result in increased visual impairment.

Epinephrine eye drops are also associated with side effects such as conjunctival congestion, pain at the eyebrow and allergic blepharoconjunctivitis. The eye drops sometimes bring about increased intraocular pressure due to mydriasis.

Recently, $\beta$-blockers have become promising in this field, and timolol maleate, levobunolol hydrochloride and betaxolol hydrochloride are commercially available. These drugs are $\beta$-adrenergic antagonists that are believed to work by blocking the $\beta$-adrenergic receptors in the ciliary epithelium and, thereby, decrease the production of aqueous humor, the clear fluid that circulates in the eye.

Drug therapy for glaucoma typically comprises topically instilled and/or orally administered medicines. Pilocarpine, epinephrine (and its prodrug form), and $\beta$-blockers are frequently used as topical drugs and carbonic anhydrase inhibitors are used via systemic administration. Because of the incidence of significant side-effects associated with conventional medical therapy for glaucoma, there is a serious problem with patient compliance. The discomfort of taking these medicines results in patients not following their treatment schedules.

The problems associated with present commercially available drugs has encouraged development of new agents for the treatment of glaucoma. There is thus a need for the development of new agents which avoids the shortcomings and problems of the presently available medicaments.

SUMMARY OF THE INVENTION

According to the present invention there is provided a method of treating glaucoma and intraocular hypertension in a mammal comprising administering to the eye of the mammal or systemically, in an amount effective to reduce intraocular pressure, compounds which act as agonists at $\beta_3$-adrenergic receptors (also known as $\beta_3$-adrenoceptors). Such receptors have been described for example by J R S Arch et. al., Nature, 309, 163–165 (1984); C. Wilson et. al., Eur J. Pharmacol., 100, 309–319 (1984); L J Emorine et. al, Science 245, 1118–1121 (1989); and A. Bianchetti et. al. Br. J. Pharmacol., 100, 831–839 (1990).

$\beta_3$-adrenoceptors belong to the family of adrenoceptors which mediate the physiological actions of the hormones adrenaline and noradrenaline. Sub-types of the adrenoceptors, $\alpha_1$-, $\alpha_2$-, $\beta_1$-, $\beta_2$-, and $\beta_3$- can be identified on the basis of their pharmacological properties and physiological effects. Chemical agents which stimulate or block these receptors (but not $\beta_3$) are widely used in clinical medicine. More recently, emphasis has been placed upon specific receptor selectivity in order to reduce side effects caused, in part, by interactions with other receptors.

$\beta_3$-adrenoceptors are known to occur in adipose tissue and the gastrointestinal tract. $\beta_3$-adrenoceptor agonists have been found to be particularly useful as thermogenic anti-obesity agents and as anti-diabetic agents. Compounds which act as agonists at $\beta_3$-adrenoceptors may be identified using standard tests.(see for instance C Wilson et. al., supra).

The present invention is directed to the use of $\beta_3$-agonists compounds which have a formula according to compounds I–IX which are described in the present specification.

It has now been found unexpectedly that compounds of Formulae I–IX which act as agonists at $\beta_3$ adrenoceptors may be useful for the treatment of glaucoma and/or ocular hypertension by topical or systemic administration in mammals.

Accordingly the present invention provides a method of treatment of a mammal, including man, suffering from glaucoma or ocular hypertension which comprises administering to the subject an effective amount of a compound of Formulae I–IX which acts as an agonist at $\beta_3$-adrenoceptors.

In a preferred aspect of the present invention, there is provided a method of treatment of a mammal, including man, suffering from a condition of glaucoma and/or ocular hypertension which comprises topically administering to the subject an effective amount of a compound of Formulae I–IX which acts as an agonist at $\beta_3$-adrenoceptors.

In a particularly preferred aspect of the present invention, there is provided a method of treatment of a mammal, including man, suffering from a condition of glaucoma and/or ocular hypertension which comprises systemically administering to the subject an effective amount of a compound of Formulae I–IX which acts as an agonist at $\beta_3$-adrenoceptors.

References in this specification to treatment include prophylactic treatment as well as treatment for the acute alleviation of symptoms.

Preferred compounds for use according to the invention are those compounds which act as agonists at $\beta_3$-adrenoceptors described in published European Patent Specification Nos. 6735, 21636, 23385, 25331, 28105, 29320, 40000, 40915, 51917, 52963, 61907, 63004, 66351, 68669, 70133, 70134, 82665, 89154, 91749, 94595, 95827, 99707, 101069, 102213, 139921, 140243, 140359, 142102, 146392, 164700, 170121, 170135, 171519, 171702, 182533, 185814, 196849, 198412, 210849, 211721, 233686, 236624, 254532, 254856, 262785, 300290, 303546, 328251, 345591, 386603, 386920, 436435, 455006, 500443, 516349, and 556880; published UK Patent Specification No. 2133986; published PCT Patent Specification Nos. 84/00956, 84/03278, 84/04091, 90/13535 and 92/18461; U.S. Pat. Nos. 4,391,826, 4,585,796; published Belgian Patent Specification No. 900983, published Japanese Patent Specification No. 86-145148, U.S. Pat. Nos. 5,061,727, 5,151,439, 4,707,497, 4,927,836 and application Ser. No. 010,973 filed Jan. 29, 1993, now abandoned.

A preferred group of $\beta_3$-adrenoceptor agonists for use according to the present invention is that represented by the Formula (I):

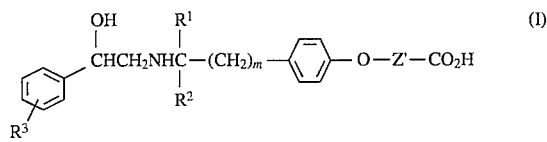

(I)

or a physiologically acceptable salt, ester or amide thereof, wherein $R^1$ and $R^2$ each independently represent a hydrogen atom or a methyl group; $R^3$ represents a hydrogen, fluorine or chlorine atom or a trifluoromethyl group; $Z'$ is an alkylene, alkenylene or alkynylene group of up to 10 carbon atoms; and m is 1,2 or 3.

Another preferred group of $\beta_3$-adrenoceptor agonists for use according to the present invention is that represented by the Formula (II):

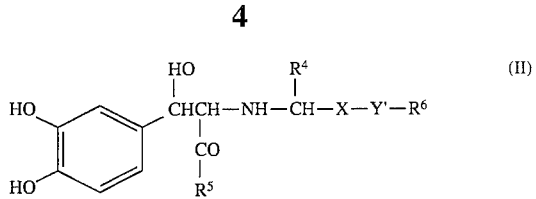

(II)

or a physiologically acceptable salt thereof, wherein $R^4$ represents a hydrogen atom or a $C_{1-4}$ alkyl or a phenyl group; $R^5$ represents a group of the formula —$OR^7$ or $NR^8R^9$; $R^6$ represents a group selected from $C_{1-3}$alkyl, cyclohexyl, phenyl (optionally substituted by one or more groups selected from $C_{1-4}$alkyl, hydroxy, methoxy, dimethylamino, trifluoromethyl, methylenedioxy or halogen atoms), naphthyl, pyridyl, furyl, thienyl or pyrrolyl; $R^7$ represents a $C_{1-4}$alkyl or carbo$C_{1-2}$alkoxymethyl group; $R^8$ represents a hydrogen atom or a methyl, ethyl or amino group; $R^9$ represents a hydrogen atom or methyl group;or the group —$NR^8R^9$ form a cyclic amino group of the formula:

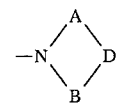

wherein A and B each independently represent a single bond or an unsubstituted straight $C_{1-3}$alkylene chain, or a straight $C_{1-3}$alkylene chain substituted by carbomethoxy, hydroxymethyl or phenyl, and D is methylene, ethylene, 1,2-cyclohexylidine or 1,2-benzo; X is a single bond or a straight $C_{1-4}$alkylene chain; and Y' is a single bond, oxa, methylimino or —CONH—; or $R^4$-CH-X-Y'-$R^6$ forms a tetrahydronaphthyl group.

Yet another preferred group of $\beta_3$-adrenoceptor agonists for use according to the present invention is that represented by the Formula(III):

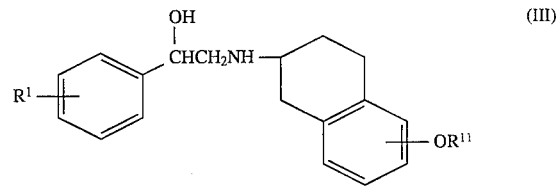

(III)

or a physiologically acceptable salt thereof, wherein $R^{10}$ represents a hydrogen or a halogen atom or a trifluoromethyl or $C_{1-4}$alkyl group; and $R^{11}$ represents a hydrogen atom or a group selected from $C_{1-4}$alkyl (optionally substituted by a $C_{3-7}$cycloalkyl, hydroxy, $C_{1-4}$alkoxy, carboxy or $C_{1-4}$alkoxycarbonyl group), $C_{3-7}$cycloalkyl or $C_{1-4}$alkanoyl.

Yet another preferred group of $\beta_3$-adrenoceptor agonists for use according to the present invention is that represented by the Formula (IV):

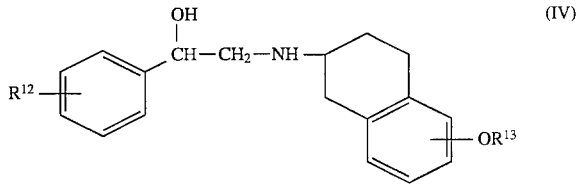

(IV)

or a physiologically acceptable salt thereof, wherein $R^{12}$ represents hydrogen, halogen, a trifluoromethyl or a lower alkyl group and $R^{13}$ represents hydrogen, a lower alkyl group not substituted or substituted by a cycloalkyl group containing 3 to 7 carbon atoms, a hydroxy group, a lower alkoxy, carboxy or lower carbalkoxy group; a cycloalkyl group containing 3 to 7 carbon atoms; or a lower alcanoyl group.

Yet another preferred group of $\beta_3$-adrenoceptor agonists for use according to the present invention is that represented by the Formula (V):

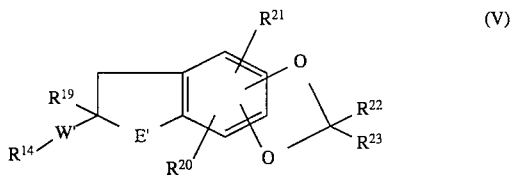

or a physiologically acceptable salt thereof, wherein $R^{14}$ is naphthyl, 5,6,7,8-tetrahydronaphth-(1 or 2)-yl and 5,8-dihydronaphth-(1 or 2)-yl; or

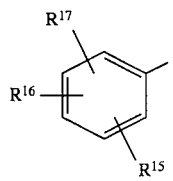

and $R^{15}$, $R^{16}$, and $R^{17}$ may be the same or different and are hydrogen, $(C_1-C_4)$alkyl, $(C_1-C_4)$alkoxy, hydroxy, halogen (chlorine, bromine, fluorine and iodine), trifluoromethyl, carboxy, hydroxy $(C_1-C_{10})$alkyl, $(C_1-C_{10})$alkoxycarbonyl, thio$(C_1-C_4)$alkyl, sulfonyl or sulfinyl; n is an integer from 1 to 3; E' is $-(CH_2)_n-$; W' is a divalent radical of

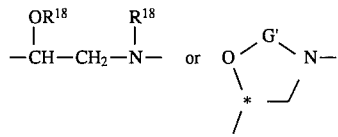

wherein $R^{18}$ is hydrogen, $(C_1-C_4)$alkyl, $(C_1-C_4)$acyl, $(C_1-C_4)$alkoxycarbonyl or benzoyl; G' is carbonyl or thiocarbonyl; $R^{19}$ is hydrogen or $(C_1-C_4)$alkyl; $R^{20}$ and $R^{21}$ may be the same or different and are hydrogen, $(C_1-C_4)$alkyl, $(C_1-C_4)$alkoxy, hydroxy, halogen (chlorine, bromine, fluorine and iodine), trifluoromethyl, carboxy, hydroxy $(C_1-C_{10})$alkyl, $(C_1-C_{10})$alkoxycarbonyl, thio$(C_1-C_4)$alkyl, sulfonyl or sulfinyl; $R^{22}$ and $R^{23}$ are hydrogen, carboxyl, $(C_1-C_{10})$alkoxycarbonyl, hydroxymethyl, $-CH_2OCH_2COOR^{24}$ or $-CH_2OCH_2CH_2OR^{24}$, wherein $R^{24}$ is hydrogen, $(C_1-C_4)$alkyl, or $CONHR^{25}$; $R^{25}$ is hydrogen, straight or branched $(C_1-C_{10})$alkyl or 2-methoxy-1-ethyl; with the proviso that $R^{22}$ and $R^{23}$ may not both be hydrogen; and the pharmacologically acceptable salts or esters thereof; the racemic mixtures thereof or the diastereomeric mixtures thereof.

Yet another preferred group of $\beta_3$-adrenoceptor agonists for use according to the present invention is that represented by the Formula (VI):

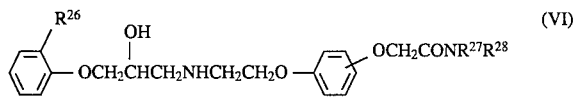

wherein $R^{26}$ is hydrogen or fluoro; $R^{27}$ is phenyl optionally bearing a substituent selected from the group consisting of halogen, $(C_1-C_4)$alkyl, $(C_1-C_4)$alkoxy, trifluoromethyl, and nitro, $(C_3-C_6)$cycloalkyl, $(C_1-C_4)$alkyl in which the carbon atom linked to the nitrogen of $NR^{27}R^{28}$ bears one or two hydrogens or is $(C_3-C_4)$alkenyl, either of which latter groups may optionally bear a substituent selected from the group consisting of hydroxy, $(C_1-C_4)$alkoxy, phenyl and chlorophenyl; and $R^{28}$ is hydrogen, methyl or ethyl; or a pharmaceutically acceptable acid addition salt thereof.

Yet another preferred group of $\beta_3$-adrenoceptor agonists for use according to the present invention is that represented by the Formula (VII):

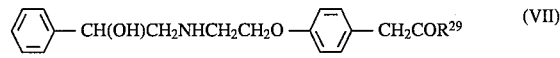

wherein $R^{29}$ is OH or $NH_2$ and pharmaceutically acceptable salts.

Yet another preferred group of $\beta_3$-adrenoceptor agonists for use according to the present invention is that represented by the Formula (VIII):

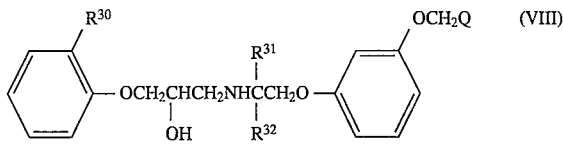

wherein $R^{30}$ is H or F; $R^{31}$ and $R^{32}$ are H or alkyl; Q is $CH_2OH$ or a group $-COR^{33}$ in which $R^{33}$ is OH, $NH_2$ or alkoxy and pharmaceutically acceptable salts.

Yet another preferred group of $\beta_3$-adrenoceptor agonists for use according to the present invention is that represented by the Formula (IX):

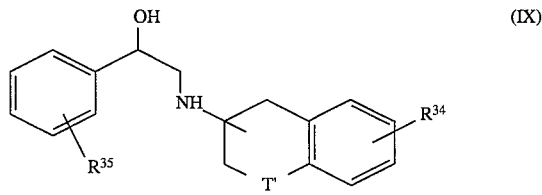

wherein $R^{34}$ is lower alkoxy substituted by COOH or carboxyalkoxy; $R^{35}$ is H or halogen; T' is $-(CH_2)_v-$; v is 0,2 or 3 and pharmaceutically acceptable salts.

Particularly preferred $\beta_3$-adrenoceptor agonists and physiologically acceptable salts or solvates thereof for use according to the present invention are listed below. It will be appreciated that where the above compounds of Formulae (I) to (IX) and the following specific compounds are optically active, the use of individual enantiomers, diastereoisomers or mixtures thereof, including racemates, is also considered to be within the scope of the present invention.

N-[2-(4-carbomethoxymethoxyphenyl)-1-methylethyl]-2-hydroxy-2-(3- chlorophenyl)ethanamine (BRL 35135);

N-[2-(4-carboxymethoxyphenyl)-1-methylethyl]-2-hydroxy-2-(3-chlorophenyl)ethanamine (BRL 37344);

DL-threo-3-(3,4-dihydroxyphenyl)-N-(3-(4-fluorophenyl) propyl) serine pyrrolidine amide (SM-11044);

5,6,7,8-tetrahydro-7-[(2-hydroxy-2-phenylethyl)amino]-2-naphthalenol (SR-58306);

2-[[7-ethoxycarbonylmethoxy-1,2,3,4-tetrahydronaphth-2-yl]amino]-1-[3- chlorophenyl]ethanol (SR-58380);

7-[[2-(3-chlorophenyl)-2-hydroxyethyl]amino]-5,6,7,8-tetrahydro-2-naphthalenol (SR-58572);

N-[(2S)-7-ethoxycarbonylmethoxy-1,2,3,4-tetrahydronaphth-2-yl]-(2R)-2-(3-chlorophenyl)-2-hydroxyethanamine (SR-58611);

N-[[7-carboxymethyl]-1,2,3,4-tetrahydronaphth-2-yl]-2-hydroxy-2-(3-chlorophenyl)ethylamine (SR-58398);

(R,R)-7-[[2-(3-chlorophenyl)-2-hydroxyethyl]amino]-7,8-dihydro-6H-indeno[4,5-d]-1,3-dioxole-2,2-dicarboxylic acid disodium salt;

(R,R)-7-[2-(3-chlorophenyl)-2-hydroxyethyl]amino]-7,8-dihydro-6H-indeno[4,5-d]-1,3-dioxole-2,2-dicarboxylic acid diisopropyl ester;

(R)-7-[2-(3-chlorophenyl)-2-hydroxyethyl]amino]-7,8-dihydro-6H-indeno[5,6-d]-1,3-dioxole-2,2-dicarboxylic acid disodium salt;

(R,R)-6-[2-(3-chlorophenyl)-2-hydroxyethyl]amino]-5,6,7,8-tetrahydrohaphtho[2,3-d]-1,3-dioxole-2,2-dicarboxylic acid disodium salt;

(R,S)-6-[2-(3-chlorophenyl)-2-hydroxyethyl]amino]-5,6,7,8-tetrahydrohaphtho[2,3-d]-1,3-dioxole-2,2-dicarboxylic acid disodium salt;

(R,S)-5-(2-((2-(3-chlorophenyl)-2-hydroxyethyl)amino) propyl)-1,3-benzodioxole-2,2-carboxylic acid;

(S)-4-[2-(2-hydroxy-3-phenoxypropylamino)ethoxy]-N-(2-methoxyethyl)phenoxyacetamide or a pharmaceutically acceptable acid addition salt;

(S)-4-[2-(2-hydroxy-3-phenoxypropylamino)ethoxy]-N-(2-methoxyethyl)phenoxyacetamide hydrochloride;

4-[2-(2-hydroxy-2-phenylethylamino)ethoxy]phenylacetic acid;

2-p-(2-[2-hydroxy-3-phenoxypropyl)amino]ethoxy)phenol and salts thereof;

1R-2-[(3-ethoxycarbonyl)-methoxy-6,7,8,9-tetrahydro-5H-benzocyclohepten-6-yl)-amino]-1-(3-chlorophenyl)ethanol hydrochloride;

(R,R)-(4-(2-((2-(3-chlorophenyl)-2-hydroxyethyl)amino) propyl)phenoxyl-acetic acid monosodium salt.

In a further aspect, the present invention provides a therapeutic agent which comprises an effective amount of a compound which acts as an agonist at β-adrenoceptors for use in medicine, Also according to the present invention there is provided a method of treating glaucoma and ocular hypertension in humans or other mammals which comprises administering to a human or other mammal an antiglaucoma or ocular antihypertensive effective amount of a $\beta_3$ compound of the present invention.

Further, according to the present invention there are provided pharmaceutical compositions of matter comprising an effective amount of a $\beta_3$ compound of the present invention in combination with a pharmaceutically acceptable carrier.

DETAILED DESCRIPTION OF THE INVENTION

Figure 1:
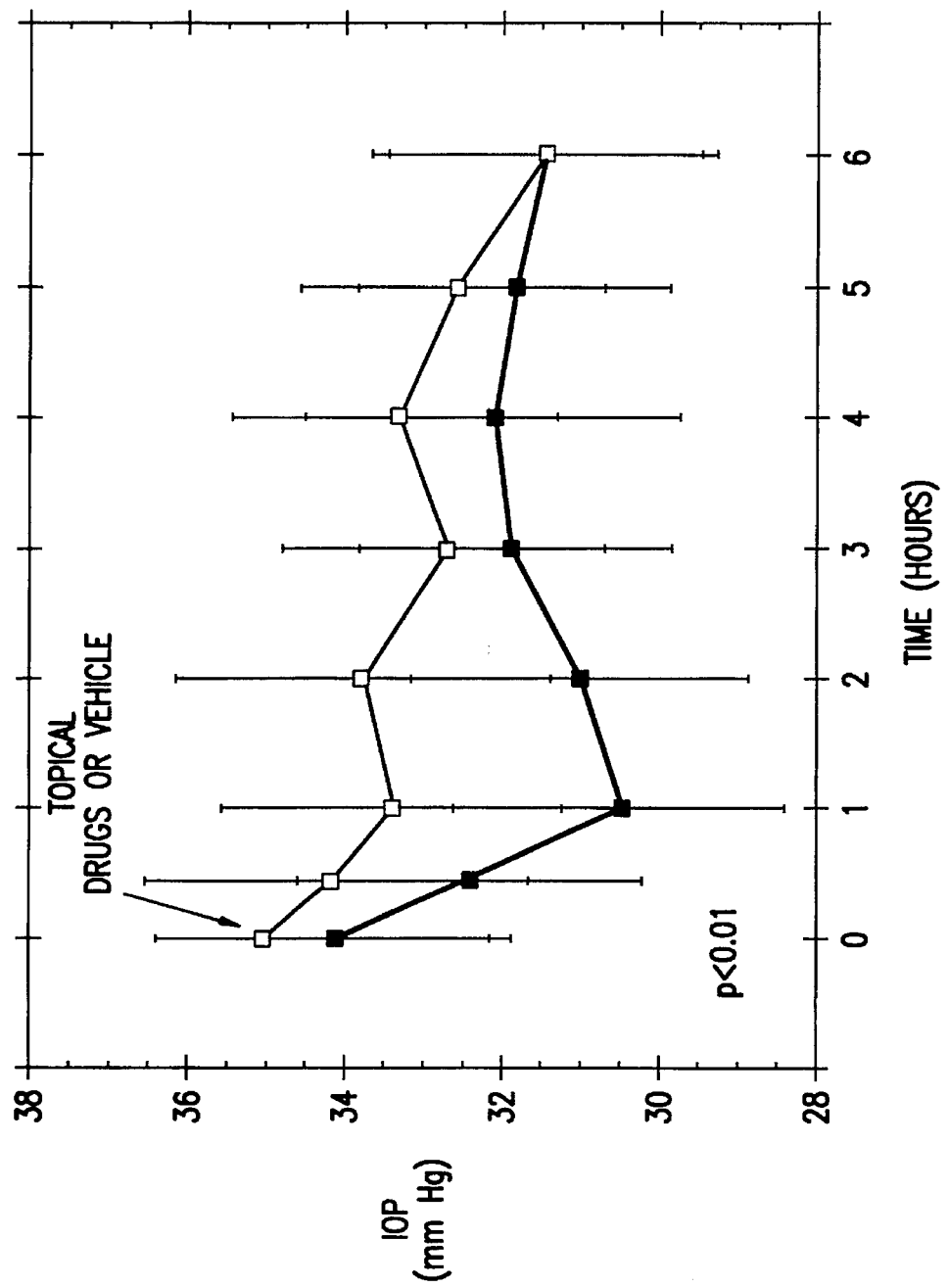
FIG. 1: The intraocular pressure lowering effect of topical administration of 50 μl of 1% (R,R)-(4-(2-((2-(3-chlorophenyl)-2-hydroxyethyl) amino ) propyl)phenoxyl-acetic acid monosodium salt to 8 glaucomatous cynomolgus monkey eyes (mean±sem).

This invention provides a method of treating glaucoma or ocular hypertension. The method comprises either topical ocular or oral dosing with a composition comprising an effective intraocular pressure reducing amount of a $\beta_3$-adrenergic agonist chosen from Formulae I to IX.

In a series of experiments in a glaucomatous monkey model, compositions according to the invention are administered topically to an animal eye and the intraocular pressure in the experimental eye is compared to controls. The procedures for the laser induced glaucoma are published in the following articles: Gaasterland D. and Kupfer C, Invest. Ophthalmol 13: 455–457(1974) and Lee PY, Podos SM, Howard-Williams JR, Severin CH, Rose AD, Siegel MJ, Curr Eye Res 4: 775–781(1985). The results of the comparative tests are presented in FIG. 1. The effect of this additional $\beta_3$adrenergic agonist on the intraocular pressure of glaucomatous monkey eyes is seen in that the topical ocular administration of 50 μl of 1%, (R,R)-(4-(2-((2-(3-chlorophenyl)-2-hydroxyethyl)amino)propyl)phenoxyl-acetic acid monosodium salt in 0.02M phosphate buffer at pH 7.4 is found to cause a statistically significant reduction in intraocular pressure compared to the vehicle control intraocular pressure at 1 hour after administration (FIG. 1).

The pharmaceutical compositions of the invention are administered in the form of ophthalmic pharmaceutical compositions adapted for topical administration to the eye, such as solutions, suspensions, ointments and solid inserts or standard pharmaceutical compositions for systemic administration, in the form of tablets, capsules or intravenous injections for both instantaneous and controlled release. Topical ophthalmic formulations of the invention may contain $\beta_3$-agonists in an amount from about 0.001 to about 15% (w/v %) and especially about 0.05 to about 5% of medicament. As a unit dosage form, an amount of $\beta_3$-agonist from between about 500 ng to 7.5 mg, preferably 0.05 mg to 2.5 mg of the active substance applied topically to the human eye. These doses can be administered as a single daily dose or on a 2 to 4 dose per day regimen. Systemically administered formulations may contain $\beta_3$-agonists in an amount from about 1 mg to about 2000 mg and especially about 5 mg to 1500 mg as a single daily dose or on a 2 to 4 dose per day regimen.

Where utilized herein, the term "controlling the elevated intraocular pressure" means the regulation, attenuation and modulation of increased intraocular tension e.g., the primary diagnostic symptom of the disease glaucoma. The term also means that the diminution, in the otherwise elevated intraocular pressure, obtained by the practice of the invention is maintained for a significant period of time as, for example, between consecutive doses of the composition of the invention.

The $\beta_3$-agonists may be employed in the composition and methods of the invention as the sole IOP lowering ingredient or may be used in combination with other mechanistically distinct IOP lowering ingredients such as β-adrenergic blocking agents, (e.g., timolol), carbonic anhydrase inhibitors, miotic agents (eg pilocarpine), epinephrine and dipivalylepinephrine, $\alpha_2$ adrenergic agonists, prostaglandins or prostaglandin analogs. For the purposes of the present invention, the term β-adrenergic blocker means a compound which by binding to $\beta_1$ or $\beta_2$ adrenergic receptors reduces or eliminates sympathetic activity or blocks the effects of exogenously administered catecholamines or adrenergic drugs mediated via these receptors. See, for example, Weiner, N., Drugs That Inhibit Adrenergic Nerves and Block Adrenergic Receptors, in The Pharmaceutical Basis of Therapeutics (ed. A. G. Goodman, L. S. Goodman, A. Gilman), Macmillan Publishing, N.Y., 1980, 6th ed., pp. 188–197.

The present invention therefore also provides a pharmaceutical formulation suitable for use in reducing intraocular pressure or for treating glaucoma which formulation comprises a novel compound of Formulae (I) to (IX) and a pharmaceutically acceptable carrier.

It will be understood that any formulation may further comprise another active ingredient such as another antiglaucoma agent for example a topical carbonic anhydrase inhibitor or a topical β-adrenergic blocking agent.

Pharmaceutically suitable salts include both the metallic (inorganic) salts and organic salts; a list of which is given in *Remington's Pharmaceutical Sciences*, 17th Edition, pg.

1418 (1985). It is well known to one skilled in the art that an appropriate salt form is chosen based on physical and chemical stability, flowability, hygroscopicity and solubility. Preferred salts of this invention for the reasons cited above include potassium, sodium, calcium, magnesium and ammonium salts.

The active drugs of this invention are most suitably administered in the form of tablets or capsules for oral administration or in the form of ophthalmic pharmaceutical compositions adapted for topical administration to the eye such as a solution, suspension, ointment, or as a solid insert. For oral administration, the drug can be employed in any of the usual dosage forms either in a comtemporaneous delivery system or sustained release form. Any number of the usual excipients or tableting aids can likewise be included. A preferred composition for topical ophthalmic administration is eye drops. Formulations of these compounds may contain from 0.001 to 15% and especially 0.05% to 5% of medicament which corresponds to dosages from between 500 ng to 7.5 mg, preferably 0.05 to 2.5 mg, generically applied to the human eye, generally on a daily basis in single or divided doses so long as the condition being treated exists. Higher dosages as, for example, about 10% or lower dosages can be employed provided the dose is effective in reducing or controlling elevated intraocular pressure.

This invention therefore further provides a sterile pharmaceutical formulation adapted for topical administration to the eye which formulation comprises a compounds of Formulae (I) to (IX) and a carrier suitable for topical administration. These herein before described dosage values are believed accurate for human patients and are based on the known and presently understood pharmacology of the compounds, and the action of other similar entities in the human eye. As with all medications, dosage requirements are variable and must be individualized on the basis of the disease and the response of the patient.

For topical administration, pharmaceutically acceptable carriers are, for example, water, mixtures of water and water-miscible solvents such as lower alkanols or arylalkanols, conventional phosphate buffer vehicle systems, isotonic boric acid vehicles, isotonic sodium chloride vehicles, isotonic sodium citrate vehicles, isotonic sodium acetate vehicles, vegetable oils, polyalkylene glycols, petroleum based jelly, as well as aqueous solutions containing ethyl cellulose, carboxymethylcellulose, hydroxypropylmethylcellulose, hydroxyethylcellulose, carbopol, polyvinyl alcohol, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying agents, wetting agents, bodying agents and the like, as for example, polyethylene glycols 30, 200, 300, 400 and 600, carbowaxes 1,000,1,500, 4,000, 6,000 and 10,000, and polysorbate 80. Antibacterial and preservative components can also be employed in the topical ophthalmic formulation, as for example, benzalkonium chloride, and other quaternary ammonium preservative agents, phenylmercuric salts, sorbic acid, chlorobutanol, disodium edetate, thimerosal, methyl and propyl paraben, benzyl alcohol, and phenyl ethanol. Osmotic agents and buffering ingredients which may be employed in the topical ophthalmic formulation include sodium chloride, mannitol, sodium borate, sodium acetates, sodium phosphates, gluconate buffers, sodium hydroxide and hydrochloric acid. Other conventional ingredients can be employed such as sorbitan monolaurate, triethanolamine, oleate, polyoxyethylene sorbitan 35 monopalmitylate, dioctyl sodium sulfosuccinate, monothioglycerol, thiosorbitol, ethylenediamine tetraacetic acid, and the like.

The pharmaceutical formulation may also be in the form of a solid insert such as one which after dispensing the drug remains essentially intact, or a bio-erodible insert that is soluble in lacrimal fluids or otherwise disintegrates.

What is claimed is:

1. A method of treating glaucoma or reducing intraocular pressure in a patient in need of such treatment which comprises topically administering to the eye of a mammal or systemically administering to a mammal in an amount effective to reduce intraocular pressure, a compound having the Formula (v):

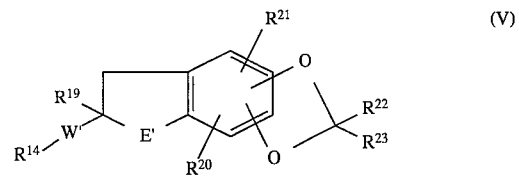

wherein $R^{14}$ is naphthyl, 5,6,7,8-tetrahydronaphth-(1 or 2)-yl or 5,8-dihydronaphth-(1 or 2)-yl; or

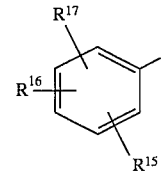

wherein $R^{15}$, $R^{16}$, and $R^{17}$ may be the same or different and are hydrogen, $(C_1-C_4)$alkyl, $(C_1-C_4)$alkoxy, hydroxy, halogen trifluoromethyl, carboxy, hydroxy$(C_1-C_{10})$alkyl, $(C_1-C_{10})$alkoxycarbonyl, thio$(C_1-C_4)$alkyl, sulfonyl or sulfinyl; n is an integer from 1 to 3; E' is —$(CH_2)_n$—; W' is a divalent radical of

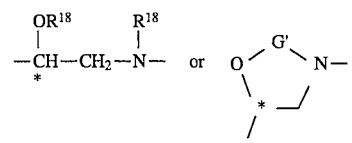

wherein * signifies an asymmetric carbon; $R^{18}$ is hydrogen, $(C_1-C_4)$alkyl, $(C_1-C_4)$acyl, $(C_1-C_4)$alkoxycarbonyl or benzoyl; G' is carbonyl or thiocarbonyl; $R^{19}$ is hydrogen or $(C_1-C_4)$alkyl; $R^{20}$ and $R^{21}$ may be the same or different and are hydrogen, $(C_1-C_4)$alkyl, $(C_1-C_4)$alkoxy, hydroxy, halogen, trifluoromethyl, carboxy, hydroxy$(C_1-C_{10})$alkyl, $(C_1-C_{10})$alkoxycarbonyl, thio$(C_1-C_4)$alkyl, sulfonyl or sulfinyl; $R^{22}$ and $R^{23}$ are hydrogen, carboxyl, $(C_1-C_{10})$alkoxycarbonyl, hydroxymethyl, —$CH_2OCH_2COOR^{24}$ or —$CH_2OCH_2CH_2OR^{24}$, wherein $R^{24}$ is hydrogen, $(C_1-C_4)$alkyl, or $CONHR^{25}$, $R^{25}$ is hydrogen, straight or branched $(C_1-C_{10})$alkyl or 2-methoxy-1-ethyl; with the proviso that $R^{22}$ and $R^{23}$ may not both be hydrogen; or the pharmacologically acceptable salts or esters thereof; the racemic mixtures thereof or the diastereomeric mixtures thereof.

2. A method as defined in claim 1 wherein the compound is (R,R)-7-[[2-(3chlorophenyl)-2-hydroxyethyl] amino]-7,8-dihydro-6H-indeno[4,5-d]-1,3-dioxole-2,2-dicarboxylic acid disodium salt.

* * * * *